United States Patent [19]

Krsek

[11] Patent Number: 4,507,242

[45] Date of Patent: Mar. 26, 1985

[54] MANUFACTURE OF ANDROSTANDIONE

[75] Inventor: George Krsek, Culver, Ind.

[73] Assignee: Progenics, Inc., New York, N.Y.

[21] Appl. No.: 598,539

[22] Filed: Apr. 10, 1984

[51] Int. Cl.$^3$ .............................................. C07J 1/00
[52] U.S. Cl. ................................................. 260/397.3
[58] Field of Search ..................................... 260/397.3

[56] References Cited

U.S. PATENT DOCUMENTS 4,230,625  10/1980  Despreaux ..................... 260/397.1

OTHER PUBLICATIONS

Chemical Abstracts 90 (1979).

*Primary Examiner*—Elbert L. Roberts
*Attorney, Agent, or Firm*—Ostrolenk, Faber, Gerb & Soffen

[57] ABSTRACT

5-β-androstandione is produced in high yield by contacting androstendione with a palladium catalyst and thereafter recovering the 5-β-androstandione thus produced.

11 Claims, No Drawings

MANUFACTURE OF ANDROSTANDIONE

BACKGROUND OF THE INVENTION

5-β-hydroxy-etiocholanolone, 5-β-androstan-3β-ol-17-one, a compound which can be used for the treatment of diabetes, is produced by converting androstendione to androstandione and thereafter converting the androstandione to the etiocholanolone. In the previously known conversions of the androstendione to androstandione, the resulting product is a mixture of 5-β-androstandione and 5-β-androstandione. The 5-β-androstandione is about 75% of the reaction product and in order to separate the 5-β isomer, it is necessary to undertake numerous laborious and time-consuming separation steps. A method in which the reaction is stereospecific to produce a much greater percentage of the β-androstandione isomer is clearly desirable.

It is accordingly the object of this invention to provide a new method for the production of androstandione so that a much greater yield of the β isomer in the 5-α and 5-β mixture reaction product is realized.

SUMMARY OF THE INVENTION

This invention relates to the production of 5-β-androstandione and more particularly to the manufacture of the 5-β-androstandione in a stereospecific manner by contacting androstendione with a palladium catalyst. In accordance with the present invention, the 5-β isomer is produced such that it is about 95% of the androstandione produced and can be easily separated from the reaction mixture by recrystallization.

DESCRIPTION OF THE INVENTION

In accordance with the present invention, 5-β-androstandione is stereospecifically prepared by contacting androstendione with a palladium catalyst and thereafter recovering the 5-β-androstandione thus produced. The palladium catalyst can be palladium itself or can be a salt, oxide or complex of palladium. Best yields have been obtained with the use of palladium metal and it is therefore preferred that when starting with a palladium salt, oxide or complex, it be treated to reduce the palladium material to palladium such as, for example, by contacting the palladium salt, oxide or complex with hydrogen to cause a reduction of the palladium material to palladium. Similarly, when using palladium itself, it is also preferred to contact the palladium with hydrogen to ensure that the maximum amount of the palladium is present as the metal. A catalytic amount of the palladium is employed in the process and this can generally range from about 0.3-2.5 parts by weight of palladium metal per 100 parts of the androstendione to be converted. Preferably, about 0.5-0.75 part of palladium metal is used.

For ease in separating the catalyst from the reaction mixture, it is preferred to employ the palladium on a reaction inert support. Known palladium support solid material, such as charcoal or calcium carbonate, can be employed and the palladium can constitute about 0.5 weight percent to saturation of the supported catalyst, preferably about 3-7 weight percent.

The reaction is preferably carried out in a reaction inert solvent such as pyridine, substituted pyridines and the like. The amount of the solvent can range from about 150-1,000 milliliters or more, preferably about 300-500 ml, per 100 grams of the androstendione reactant.

The androstendione is contacted with the palladium catalyst and hydrogen for a time sufficient to convert the androstendione to androstandione. The reaction time can be about 0.1-10 hours or more and is preferably about 1.5-2.5 hours.

After the reaction is complete, the catalyst can be removed, for example, by filtration. The desired 5-β-androstandione can then be recovered in high yield by recrystallizing the desired product in a suitable recrystallization solvent or solvent mixture such as, for example, acetone, acetone-petroleum ether mixture and isopropyl alcohol-water.

The following non-limiting example illustrates the present invention. 12 grams of a palladium on charcoal containing about 5% by weight palladium was mixed with 400 ml of pyridine on a stirred pressure vessel. The air in the vessel was replaced with hydrogen and stirred for 0.5 hour to ensure that the maximum amount of palladium was in the form of palladium metal. 100 grams of androstendione was then added and the reaction mixture stirred under a hydrogen atmosphere for two hours. The catalyst was filtered off and the filtrate was evaporated to dryness. The resulting solids were then dissolved in an isopropanol-water mixture which was thereafter cooled to about 5° C. to precipitate solids. The resulting solids were recovered by filtration. The product had a melting point of 131°–132° C. and $[\alpha]_D^{25}$ of 110° and the yield was 72 grams.

Various changes and modifications can be made in the process of the present invention without departing from the spirit and scope thereof. The embodiments which were described herein were for the purpose of illustration only and were not intended to limit the invention. Unless otherwise specified, all temperatures are in degrees Centigrade and all parts and percentages are by weight throughout this specification and claims.

What is claimed is:

1. A method for the stereospecific preparation of 5-β-androstandione which comprises catalytically hydrogenating androstendione with a palladium catalyst and thereafter recovering the 5-β-androstandione thus produced.

2. The method of claim 1, wherein the palladium catalyst is palladium.

3. The method of claim 2, wherein the palladium catalyst is carried on a reaction inert support.

4. The method of claim 3, wherein the amount of palladium is about 0.3-2.5 parts per 100 parts of androstendione.

5. The method of claim 4, wherein the amount of palladium is about 0.5-0.75 parts per 100 parts of androstendione.

6. The method of claim 4, wherein the contacting is effected in a reaction inert solvent.

7. The method of claim 6, wherein the reaction inert solvent is pyridine.

8. The method of claim 6, wherein the palladium catalyst is contacted with hydrogen prior to contacting the androstendione with the catalyst.

9. The method of claim 6, wherein the 5-βandrostandione produced is recrystallized.

10. The method of claim 9, wherein the 5-β-androstandione produced is recrystallized in aqueous iospropanol.

11. The method of claim 1, wherein 10-15 parts of a palladium on charcoal catalyst containing about 3-7% palladium is mixed with pyridine and contacted with hydrogen, androstendione and hydrogen are contacted with the resulting palladium on charcoal in pyridine, the supported palladium catalyst is separated by filtration, the resulting filtrate is evaporated to dryness and the resulting solids are recrystallized in aqueous isopropanol.

* * * * *